United States Patent
Clarke

(10) Patent No.: US 6,617,124 B1
(45) Date of Patent: Sep. 9, 2003

(54) 7-ALKOXYCOUMARINS AS CYTOCHROME P450 SUBSTRATES

(75) Inventor: Stephen Edward Clarke, Hemel Hempstead (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/646,279

(22) PCT Filed: Apr. 28, 1999

(86) PCT No.: PCT/EP99/03032

§ 371 (c)(1),
(2), (4) Date: Jul. 26, 2001

(87) PCT Pub. No.: WO99/58710

PCT Pub. Date: Nov. 18, 1999

(30) Foreign Application Priority Data

May 8, 1998 (GB) .............................................. 9810016

(51) Int. Cl.[7] ................................................ C12Q 1/26
(52) U.S. Cl. ........................................ 435/25; 549/289
(58) Field of Search ............................. 435/25; 549/289

(56) References Cited

FOREIGN PATENT DOCUMENTS

| DE | 1929839 | 12/1969 |
| GB | 1226896 | * 3/1971 |

OTHER PUBLICATIONS

Hanmantgad, H.S., Kulkarni, M.V., Patil, V.D., Indian Journal of Chemistry vol. 24, 1985 pp. 459–461, XP002115751.

A.Prasanna de Silva, H.Q. Nimql Gunaratine, P.L. Mark Lynch, A.J. Patty, G.L. Spence, Journal of the Chemical Society, Perkin Transactions 2, 1993, p. 1611 XP002115752 p. 1612; figure 1.

C.L. Crespi, V.P. Miller, B.W. Penman, Analytical Biochemistry, vol. 248, 1997, pp. 188–190, XP002115753.

Koymans L., et al. Chemical Research In Toxicology, vol. 5, No. 2, Mar. 1, 1992 pp. 211–219, XP000568353.

J. Krejcoves, J.Drobnik, J. Jokl, J.Kalal, Collection of Czechoslovak Chemical Communications vol. 44, 1979, pp. 2211–2220, XP002115755 p. 2213; examples 15–18.

Hodgkiss R.J.; Jones G.W.; Long, A.; Middleton, R.W.; Parrick, J. Stratford, M.R.L.; Wardman, P.; Wilson, G.D.; Journal of Medicinal Chemistry, vol. 34, No. 7, 1991, pp. 2268–2274, XP002115756 p. 2270.

(List continued on next page.)

*Primary Examiner*—Ralph Gitomer
(74) *Attorney, Agent, or Firm*—Loretta J. Henderson; Mary E. McCarthy; Charles M. Kinzig

(57) ABSTRACT

Coumarin derivatives as substrates for cytochrome P450 enzyme.

5 Claims, 1 Drawing Sheet

OTHER PUBLICATIONS

Figure 1:
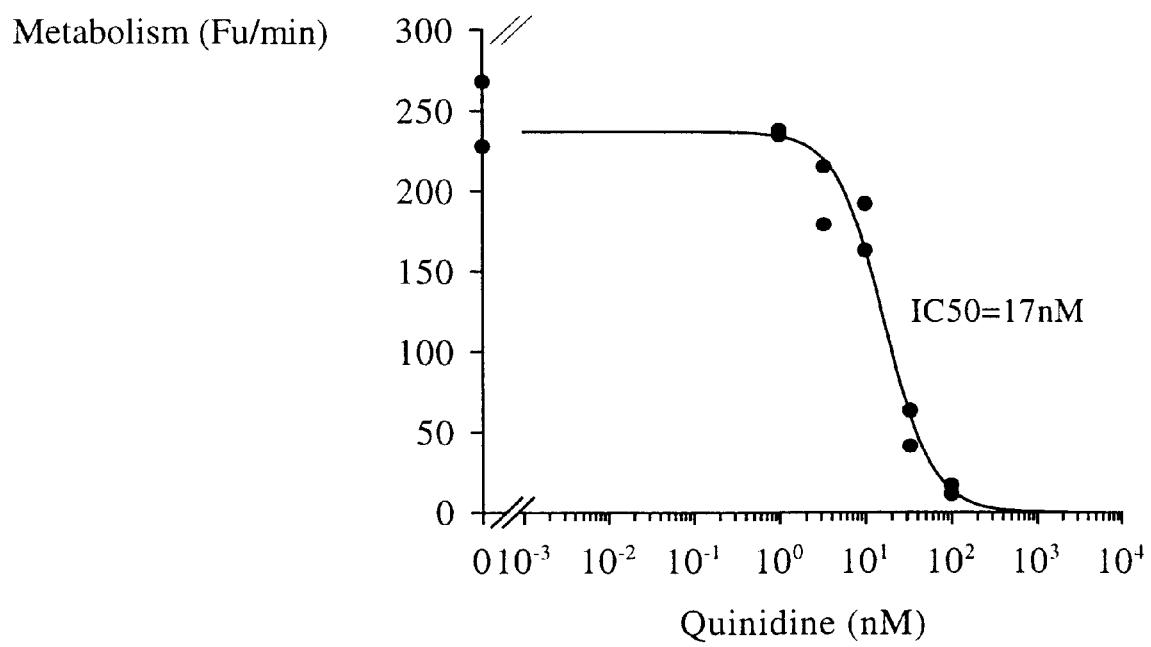

Li, M.; White, E.H.; Bioconjugate Chemistry, vol. 5, No. 5, 1994, pp. 454–458, XP002115757.

Chemical Abstracts, vol. 104, No. 19, 1986 abstract No. 168321 Hanmantgad S.S.; Kulkarni, M.V.; Patil, V.D., XP002115759 abstract & Revue Roumaine De Chimie vol. 30, No. 8, 1985, pp. 735–741.

Chemical Abstracts, vol. 109, No. 19, 1988 Nagesam, M.; Raju, M.K.; Raju, M.S.; XP002115760 & Indian Journal of Pharmaceutical Sciences vol. 50, No 1, 1988, pp. 49–52.

S.V. Otton, H.K. Crewe, M.S. Lennard, G.T. Tucker, H.F. Woods, Journal of Pharmacology and Experimental Therapeutics vol. 247, 1988, pp. 242–247, XP002115758.

Nakamura et al. (2001). Coumarin substrates for cytochrome P450 2D6 fluorescence assays. Analytical Biochemistry 292, pp. 280–286.*

Onderwater et al. (1999). Design, synthesis and characterization of 7–methoxy–4–(aminomethyl)coumarin as a novel and selective cytochrome P450 2D6 substrate suitable for high through–put screening. Chem. Res. Toxicol. 12, pp. 555–559.*

Venhorst et al. (2000). Influence of N–substitution of 7–methoxy–4–aminomethylcoumarin on cytochrome P450 metabolism and selectivity. Drug Metab. Dispos. 28 (12), pp. 1524–1532.*

Venhorst et al. (2000). Evaluation of a novel high–throughput assay for cytochrome P450 2D6 using 7–methoxy–4–aminomethylcoumarin. Eur. J. Pharm. Sci. 12(2), pp. 151–158.* de Silva et al. (1993). Luminescence and charge transfer. J Chem Soc Perkin Trans. 2, pp 1611–1616.*

Mace K., Vautravers P, Granato D., Gonzalez, F., Harris C.C., Pfiefer A.M.A., In Vitro Toxicology, Development of CYP450–Expressing Human Bronchial Epithelial Cell Lines for In Vitro Pharmacotoxicological Applications, vol. 10, No. 1, pp. 85–92, 1997.

* cited by examiner

7-ALKOXYCOUMARINS AS CYTOCHROME P450 SUBSTRATES

This application is filed as a 371 application based on PCT/EP99/03032 filed Apr. 28, 1999 which claims priority to UK 9810016.7 filed May 8, 1998.

This invention relates to coumarin derivatives, processes for preparing them and their use as enzyme substrates.

The majority of metabolism based drug interactions are a result of inhibition of cytochrome P450 enzymes. Drug interactions involving individual P450 enzymes can be predicted using in vitro methods. Typical in vitro P450 enzyme assays involve incubation of an appropriate substrate with a source of enzyme. Traditionally, time consuming chromatographic methods have been used for metabolite detection in these incubations. More recently the availability of fluorimetric plate readers has facilitated the higher throughput of enzyme assays in general. Adapting P450 assays to fluorescent plate reader technology requires the identification of substrates with appropriate fluorescent products for individual enzymes. Among the xenobiotic-metabolising cytochromes P450, CPY2D6 is one of those commonly responsible for the metabolism of drugs.

3-Cyano-7-ethoxycoumarin has been described for CYP2D6 inhibition screening (Crespi et al, *Anal. Biochem.*, 1997, 248, 188–190). Other CYP2D6 substrates have also been described (Koymans et al, *Chem. Res. Toxicol.*, 1992, 5, 211–219), however these do not give fluorescent products suitable for high throughput screening.

Certain compounds have now been identified which are improved substrates for CYP2D6 and which are of use for configuring high throughput inhibition screening assays.

As a brief description of the drawings: FIG. 1 shows inhibition of 7-methoxy-4-(methylarninomcthyl)coumarin metabolism with quinidine.

According to the present invention there is provided an assay for testing for inhibitors of the enzyme CYP2D6 which comprises contacting the enzyme and a compound of formula (I):

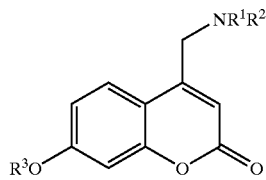

(I)

wherein $R^1$ and $R^2$ independently represent hydrogen or $C_{1-2}$alkyl and $R^3$ is $C_{1-2}$alkyl, with a test compound and measuring inhibition of O-dealkylation of the compound of formula (I) by the enzyme.

Preferably $R^1$ is hydrogen and $R^2$ is methyl $R^3$ is preferably methyl.

Generally the rate of O-dealkylation of the compound of formula (I) in the absence of test compound will be known, as will the extent of O-dealkylation at given time points. The assay may test for inhibition of O-dealkylation continuously or at specified time points.

O-dealkylation of the compound of formula (I) by CYP2D6 gives a readily quantifiable fluorescent product of formula (II):

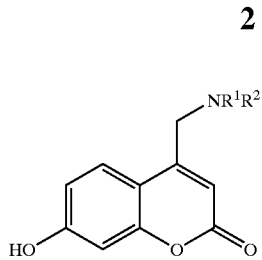

(II)

wherein $R^1$ and $R^2$ are as defined for formula (I), which can be scanned with suitable excitation and emission wavelengths, for example an excitation wavelength of 409 nm and an emission wavelength of 485 nm.

The assay may be carried out either in solution or utilising a solid support. When the assay is carried out in solution suitable solvents include methanol, acetonitrile and DMSO.

The test compound may be pre-incubated with enzyme prior to the addition of the substrate, or alternatively the substrate may be added simultaneously. Final concentrations of enzyme and substrate are calculated so as to achieve a suitable rate of processing for carrying out the assay. If desired, the reaction may be stopped, for example by addition of acid or solvent. The product may be analysed using any conventional system of fluorescence detection, for example a multi-well plate/fluorescent plate reader.

Certain of the compounds of formula (I) are novel, thus according to a further aspect of the invention there is provided a compound of formula (I), as defined above, wherein at least one of $R^1$ and $R^2$ represents methyl.

Certain of the compounds of formula (II) are novel, thus according to a further aspect of the invention there is provided a compound of formula (II), as defined above, wherein $R^1$ is methyl and $R^2$ is hydrogen or ethyl.

The compounds of formula (I) may be prepared by conventional methods, for example as shown in Scheme 1:

Scheme 1

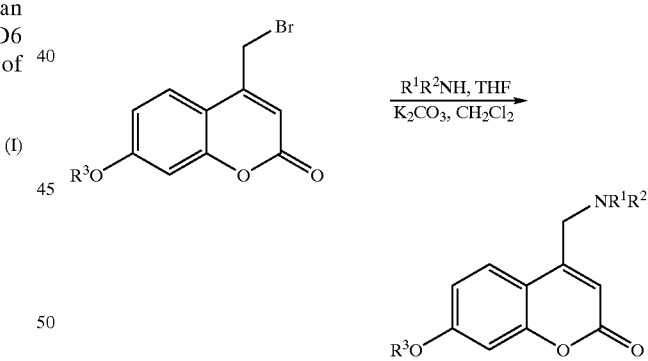

Thus according to a further aspect of the invention there is provided a process for the production of a compound of formula (I) which comprises reaction of a compound of formula (III):

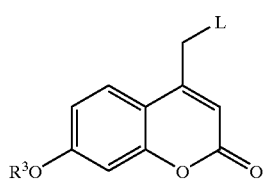

(III)

wherein L is a leaving group e.g. Br, and R³ is C₁₋₂alkyl, with a compound of formula (IV):

NHR¹R²  (IV)

wherein R¹ and R² are as defined for formula (I) provided that at least one of R¹ and R² represents methyl.

The reaction is preferably performed in the presence of a base, e.g. potassium carbonate.

Since the inhibition of cytochrome P450 enzymes is often the mechanism for drug/drug interactions, the assay according to the invention is particularly useful for identifying compounds which may give rise to adverse drug/drug interactions. The assay can therefore be used in combination with the chemical modification of test compounds to increase a test compound's potential for use as a pharmaceutical.

Thus according to further aspects of the invention there are provided a method for reducing the CYP2D6 enzyme inhibitory activity of a compound, comprising the steps of identifying the compound as an inhibitor of CYP2D6 in the assay described above; and thereafter producing a chemically modified version of the test compound in which the functionality suspected to be responsible for CYP2D6 inhibition is eliminated or changed; and novel compounds produced according to this method.

The chemical modification of test compounds according to this method can be performed using techniques well known to those skilled in the art.

The novel compounds produced according to this aspect of the invention may find application as pharmaceuticals. The fact that a compound produced according to this method will be readily identifiable as novel by performing routine literature and database searches. The pharmaceutical activity of such compounds can be readily ascertained using conventional biological screening methods known to those skilled in the art.

The invention is illustrated by the following examples.

EXAMPLE 1

Preparation of 7-Methoxy-4-(methylaminomethyl) coumarin

A solution of methylamine in tetrahydrofuran (2M, 1.10 ml) was added to an ice-cooled mixture of 4-bromomethyl-7-methoxycoumarin (0.30 g), potassium carbonate (0.5 g) and dichloromethane (10 ml). The mixture was stirred at room temperature for 2 days then added to an aqueous solution of potassium carbonate. The organic phase was washed with water, dried (MgSO₄) and evaporated. The residue was purified by chromatography on silica gel (eluent 10% methanol in dichloromethane), then crystallised from methanol to give the title compound as a white solid (0.14 g).

m.p. 109.0–109.5° C.; Found: C, 65.64; H, 5.93; N, 6.34. $C_{12}H_{13}NO_3$ requires C, 65.74; H, 5.98; N, 6.39%; δH(CDCl₃): 2.54 (s, 3H), 3.87 (s, 3H), 3.90 (d, J=1.1 Hz, 2H), 6.36 (d, J=1.1 Hz, 1H), 6.83–6.88 (m, 2H), 7.58 (d, J=8.2 Hz, 1H); mass spectrum m/z 220 (MH⁺).

EXAMPLE 2

Preparation of 7-Methoxy-4-(dimethylaminomethyl) coumarin

A mixture of dimethylamine hydrochloride (0.18 g), 4-bromomethyl-7-methoxycoumarin (0.30 g), potassium carbonate (0.5 g) and dichloromethane (10 ml) was stirred at room temperature for 2 days. The solid was filtered off and the filtrate concentrated. The residue was purified by chromatography on silica gel (eluent 5% methanol in dichloromethane), then crystallised from methanol to give the title compound as a white solid (0.145 g).

m.p. 97.0° C.; δH(CDCl₃): 2.31 (s, 6H), 3.50 (s, 2H), 3.87 (s, 3H), 6.31 (s, 1H), 6.82–6.87 (m, 2), 7.76 (d, J=8.6 Hz, 1H); mass spectrum m/z 234 (MH⁺).

Assay Methodology

Materials:
- 5 mM 7-methoxy-4-(methylarninomethyl)coumarin (i.e. 1.095 mg/mL in methanol)-store at approx. −20° C. in the dark
- 2% (w/v) NaHCO₃-store at approx. 4° C.
- 50 mM potassium phosphate buffer, pH 7.4
- Freshly prepared cofactor solution:-approx. the following per mL of 2% (w/v) NaHCO₃
  - 1.7 mg NADP, monosodium salt
  - 7.8 mg glucose-6-phosphate, monosodium salt
  - 6 Units glucose-6-phosphate dehydrogenase, Type VII from Bakers Yeast Method:
1) Mix 1 uL (5 mM) 7-methoxy-4-(methylaminomethyl) coumarin, 5 uL (50 ug) CYP2D6 microsomal protein and 214 uL buffer per incubate (giving 20 uM 7-methoxy-4-(methylaminomethyl)coumarin and 200 ug/mL protein final concentration).
2) To each well of a 96-well plate add 220 uL of incubation mix and 5 uL of test compound (or 5 uL of appropriate solvent for control wells—methanol, acetonitrile or DMSO may be used).
3) Pre-incubate the multi-well plate in the plate reader at 37° C. for 5 minutes. Pre-warm the cofactor solution at 37° C. for 5 minutes.
4) Add 25 uL cofactor solution to each well and scan with an excitation wavelength of 409 nm and an emission wavelength of 485 nm with a gain of 80. Scan for 10 cycles at 1 minute intervals.

Results

Confirmation of 7-methoxy-4-(methylaminomethyl) coumarin as a CYP2D6 substrate was achieved using quinidine, a diagnostic CYP2D6 inhibitor (Otton et al, *J. Pharm. Expt. Ther.*, 1988, 247, 242–247). With quinidine, metabolism (O-dealkylation) of 7-methoxy-4-(methylaminomethyl)coumarin was inhibited with an $IC_{50}$ of 17 nM (FIG. 1), an inhibition value typical of other, well characterised, CYP2D6 substrates.

What is claimed is:

1. An assay for testing for inhibitors of the enzyme CYP2D6 which comprises contacting the enzyme and a compound of formula (I):

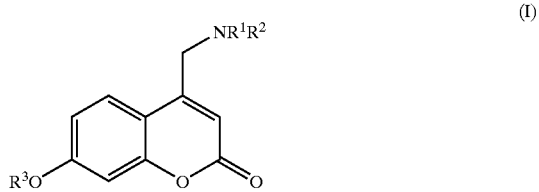

(I)

wherein R¹ and R² independently represent hydrogen or C₁₋₂alkyl and R³ is C₁₋₂alkyl, with a test compound and measuring inhibition of O-dealkylation of the compound of formula (I) by the enzyme.

2. The assay according to claim 1 wherein inhibition of O-dealkylation of the compound of formula (I) by the enzyme is measured by quantifying the compound of formula (II):

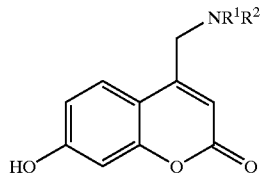 (II)
wherein $R^1$ and $R^2$ are as defined in claim 1; by fluorescence detection.
3. The assay according to claim 2 wherein the compound of formula (II) is quantified by scanning at an excitation wavelength of 409 nm and an emission wavelength of 485 nm.
4. The assay according to claim 1 wherein $R^1$ is hydrogen and $R^2$ is methyl.
5. The assay according to claim 1 wherein $R^3$ is methyl.
* * * * *